United States Patent [19]

Hunt et al.

[11] Patent Number: 5,374,518
[45] Date of Patent: Dec. 20, 1994

[54] MONOCLONAL ANTIBODY FOR DIFFERENTIATING HIV-2 FROM HIM-1 SEROPOSITIVE INDIVIDUALS

[75] Inventors: Jeffrey C. Hunt, Lindenhurst; Virender K. Sarin, Libertyville; Sushil G. Devare, Northbrook; Ilse I. E. Tribby, Chicago; Suresh M. Desai, Libertyville; James M. Casey, Gurnee, all of Ill.

[73] Assignee: Abbott Laboratories, Abbott Park, Ill.

[21] Appl. No.: 952,482

[22] Filed: Sep. 28, 1992

Related U.S. Application Data

[63] Continuation of Ser. No. 361,739, Jun. 2, 1989, abandoned, which is a continuation-in-part of Ser. No. 306,366, Feb. 3, 1989, abandoned.

[51] Int. Cl.⁵ .................. C12Q 1/70; G01N 33/53; G01N 31/22; C07K 15/06
[52] U.S. Cl. .................. 435/5; 435/7.93; 435/240.27; 435/974; 435/975; 530/388.35; 530/329; 422/56; 930/221
[58] Field of Search .......... 530/388.35, 329; 930/221; 435/5, 974, 975, 240.27, 7.93; 422/56

[56] References Cited

U.S. PATENT DOCUMENTS 5,156,949 10/1992 Luciw et al. .................. 435/5

Primary Examiner—Christine M. Nucker
Assistant Examiner—M. P. Woodward
Attorney, Agent, or Firm—Daniel W. Collins; Priscilla E. Porembski

[57] ABSTRACT

A mouse monoclonal antibody is provided which detects HIV-2 seropositive individuals and differentiates them from HIV-1 seropositive individuals. The monoclonal antibody is specific for an epitope of HIV-2 gp41 which lies outside the characterized immunodominant region. The epitope recognized by the monoclonal antibody has the amino acid sequence HTTVPW.

12 Claims, 1 Drawing Sheet

MONOCLONAL ANTIBODY FOR DIFFERENTIATING HIV-2 FROM HIM-1 SEROPOSITIVE INDIVIDUALS

This application is a continuation of application Ser. No. 07/361,739, filed Jun. 2, 1989, abandoned, which is a continuation-in-part of application Ser. No. 07/306,366, filed Feb. 3, 1989, abandoned.

BACKGROUND OF THE INVENTION

1. Field of the Invention

The present invention relates to the detection of exposure to HIV (Human Immunodeficiency Virus), the etioliogical agent of Acquired Immunodeficiency Syndrome (AIDS). In particular, a mouse monoclonal antibody, H37c94, and its epitope within HIV-2 gp41 are provided which form the basis of an immunoassay used to differentiate those individuals exposed to the HIV-2 virus from those exposed to the HIV-1 virus.

2. Description of Related Art

The nucleotide sequence of the proviral genome has been determined for several HIV isolates, including HIV-1 strains HTLV-III (Ratner et al., Nature (1985) 313:277); ARV-2 (Sanchez-Pescador et al., Science (1985) 227:484); LAV (Wain-Hobson et al., Cell (1985) 40:9); and CDC-451 (Desai et al., Proc. Natl. Acad. Sci. USA (1986) 83:8380). The nucleotide sequence of the HIV-2 ROD isolate was reported by Guyader et al. (Nature (1987) 326:662). The HIV-2 NIHZ isolate was reported by Zagury et al. (PNAS (1988) 85:5941–5945). Additional HIV sequences are found in Meyers et al., *Human Retroviruses and AIDS 1988, A Compilation and Analysis of Nucleic Acid and Amino Sequences* (Los Alamos National Laboratory, Los Alamos, N. Mex.).

One of the key serological targets for detection of HIV-1 infection is the transmembrane protein (TMP), gp41. Antibodies to this protein are among the first to appear at seroconversion, and the immune response to gp41 apparently remains relatively strong throughout the course of the disease as evidenced by the near universal presence of anti-gp41 antibodies in asymptomatic as well as all other clinical stages of AIDS. The bulk of the antibody response to the protein is directed toward a well characterized immunodominant region (Chang et al., Bio/Technology (1985) 3:905–909), broadly defined between amino acids 578 thru 613 (numbering by Meyers et al., for the HXB2 isolate). Specific, small sequences within the immunodominant region have been identified as forming the key immunogenic sequences, including RILAVERYLKDQQLLGIWGCS in which arg-1, ile-2, and lys-10 each play important roles in maintaining antigenicity of the peptide (Wang et al., Proc. Natl. Acad. Sci. U.S.A. (1986) 83:6159–6163), LGLWGCSGKLIC in which both cys residues appear to play key roles in maintaining antigenicity of the peptide (Gnann et al., J. Virology (1987) 61:2639–2641), and SGKLICTTAVPWNAS which may comprise an epitope hidden in the native virus but which is exposed and immunogenic during the course of the disease (Narvanen et al., AIDS (1988) 2:119–123). A human monoclonal antibody was raised which maps to the sequence GIWGCSGKLIC providing additional support for the central role this sequence may play as an immunogen (Banapour et al., J. Immunol. (1987) 139:4027–4033).

Other regions of gp41 apparently play only minor roles, if at all, in eliciting an immune response (Gnann et al., J. Infect. Diseases (1987) 156:261–267; and Windheuser and Wood, Gene (1988) 64:107–119), and have not been identified as being diagnostically useful.

Much less is known concerning the immunodominant epitope(s) of HIV-2 transmembrane protein, referred to as HIV-2 gp41 in this application, and research has been directed primarily toward using the immunodominant region of the protein as a serological target for differentiating exposure to HIV-2 from HIV-1. Gnaan et al. (Science (1987) 237:1346–1349) used a portion of the HIV-2 ROD immunodominant region in a synthetic peptide NSWGCAFRQVC, to detect antibody to HIV-2 and differentiate it from antibody to HIV-1. In addition, Cot et al. (AIDS *Research and Human Retroviruses* (1988) 4:239–241) also used immunodominant region peptides to differentiate human antibodies to HIV-2 gp41 from HIV-1 gp41. The HIV-2 peptide used was the sequence RVTAIEKYLQDQARLNSW-GCAFRQVC. In both studies, the region utilized ended at the second cysteine residue. In neither case, nor in any other report, has the HIV-2 sequence HTTVPW been shown to have any diagnostic value as a serological target or an antigen for a monoclonal antibody.

SUMMARY OF THE INVENTION

The present invention provides a monoclonal antibody characterized by its specificity for an epitope on HIV-2 gp41 substantially having the amino acid sequence HTTVPW. The present invention also provides a hybridoma cell line which produces the monoclonal antibody. In a preferred embodiment, a murine derived hybridoma cell line ATCC HB10012 produces the monoclonal antibody H37c94.

The present invention also provides a method for differentiating exposure of an individual to HIV-2 from exposure to HIV-1. The method comprises contacting a biological sample from the individual with an antigen including an epitope substantially having the amino acid sequence HTTVPW linked to an amino acid sequence comprising substantially the region from amino acid 578 to amino acid 603 of HIV-2 and an antibody specific to the epitope, whereby an antigen antibody complex is formed; and determining the amount of the complex formed as an indication of exposure to HIV-2.

In another aspect of the invention, the monoclonal antibody can be utilized as a probe for the detection of anti-HIV-2 antibodies in a biological sample.

DETAILED DESCRIPTION OF THE INVENTION

Figure 1:
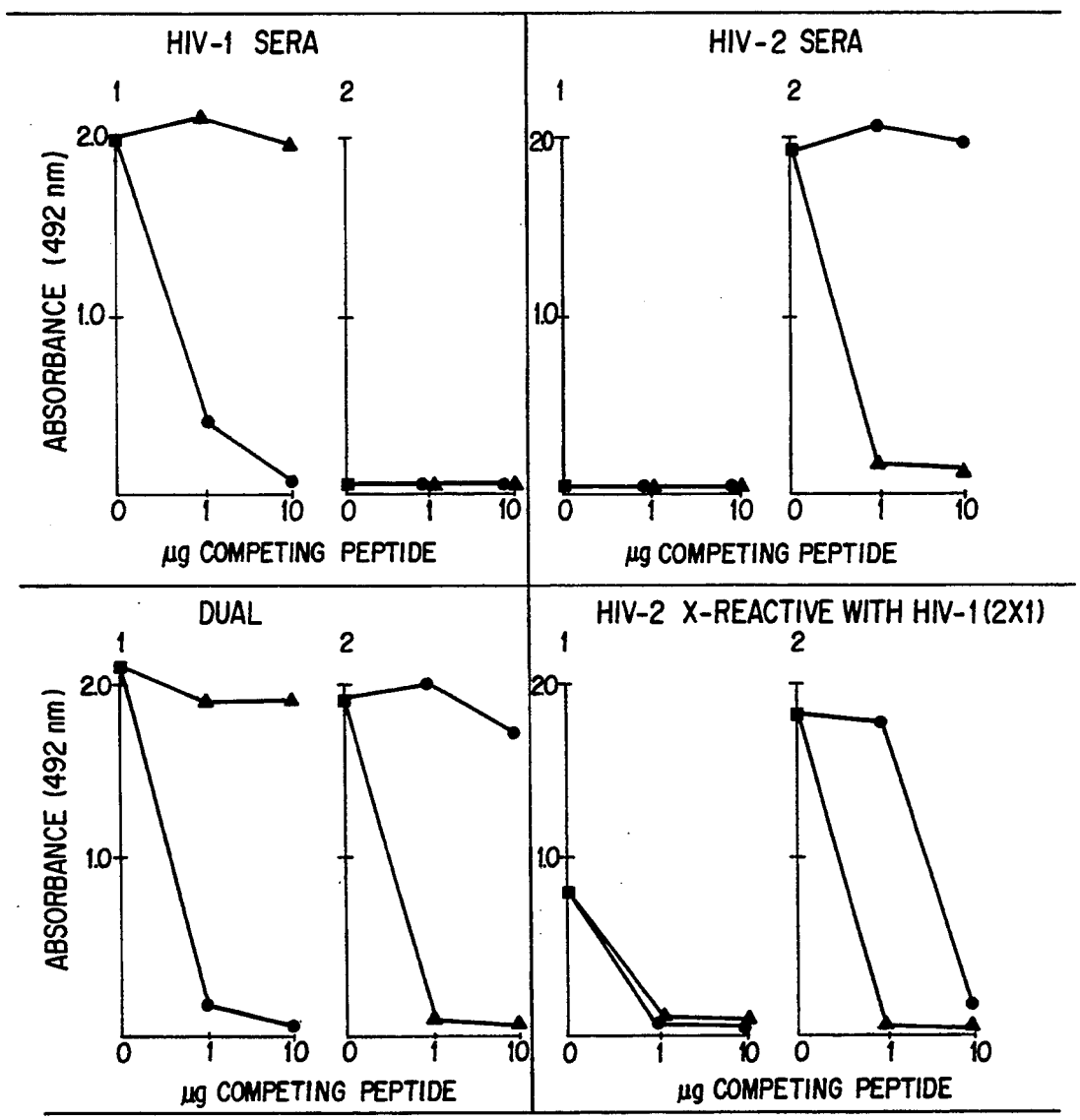
FIG. 1 illustrates the reactivity of various types of sera in a peptide inhibition assay.

The present invention provides a monoclonal antibody characterized by its specificity for an epitope on HIV-2 gp41 substantially having the amino acid sequence HTTVPW. The term "substantially" includes any related sequence having conserved or non conserved amino acid changes that is still recognized by the monoclonal antibody.

In another of its aspects, the present invention provides a hybridoma cell line which produces the monoclonal antibody of the invention. In a preferred embodiment, a murine derived hybridoma cell line ATCC HB10012 produces the monoclonal antibody H37c94.

The present invention also provides a method for differentiating exposure of an individual to HIV-2 from exposure to HIV-1. The method comprises contacting a biological sample from the individual with an antigen including an epitope substantially having the amino acid sequence HTTVPW linked to an amino acid sequence comprising substantially the region from amino acid 578 to amino acid 603 of HIV-2 and an antibody specific to the epitope, whereby an antigen antibody complex is formed; and determining the amount of the complex formed as an indication of exposure to HIV-2.

The antigen used in the method comprises inactivated whole virus, or partially purified native, synthetic, or recombinantly-produced HIV-2 gp41. The term "substantially", as used in the amino acid sequence linked to the epitope, includes any sequence having amino acid conserved or non conserved changes, as well as the addition or deletion of amino acids, that still detect HIV-2 gp41 human antibodies.

In a preferred embodiment, the method utilizes H37c94 as the antibody specific to the epitope substantially having the amino acid sequence HTTVPW. The monoclonal antibody H37c94 competes with those samples containing antibody to HIV-2 gp41 for binding to the antigen.

In another aspect of the invention, monoclonal antibody H37c94 can be utilized as a probe for the detection of anti-HIV-2 gp41 antibodies in a biological sample. In a preferred embodiment, a test sample can be mixed with labeled H37c94, followed by the addition of recombinant HIV-2 p41 fixed to a solid support. The absence of bound labeled H37c94 results in a reduction of absorbance and indicates the presence of anti-HIV-2 p41 antibodies in the test sample. Other embodiments of assays which complete H37c94 with human anti-HIV-2 antibodies are known to those skilled in the art.

Biological samples which are easily tested by the method of the present invention include human and animal body fluids such as whole blood, serum, plasma, cerebrospinal fluid and lymphocyte or cell culture supernatants.

Solid supports which can be used in immunoassays of the invention include wells of reaction trays, test tubes, polystyrene beads, strips, membranes, microparticles, and other solid matrices known to those skilled in the art.

Any label capable of producing a detectable signal or an enzyme amplification system can be used in immunoassays of the invention. Representative labels include enzymatic, radioisotopic, fluorescent and chemiluminescent labels. Alternatively, specific binding pairs can be utilized, wherein one member is attached to an antibody of the inventive assays and the other member is attached to a detectable label. For example, hapten/labeled anti-hapten systems such as a biotin/labeled antibiotin system can be used. In addition, one can employ a labeled specific binding protein for the antibody which, for example, can be labeled second antibody or labeled Protein A. Where the monoclonal antibody is derived from a murine source, a labeled anti-mouse immunoglobulin specific for the monoclonal antibody can be used. One can also utilize a labeled anti-idiotype antibody to detect the monoclonal antibody described herein.

In addition, reagents for the assays of the invention are ideally suited for preparation of a kit. Such a kit comprises carrier means being compartmentalized to receive in close confinement, one or more container means such as vials, bottles, test tubes and the like. Each of the container means comprises one of the separate elements to be used in the immunoassays of the invention.

Cell line H37c94 was deposited at the American Type Culture Collection, 12301 Parklawn Drive, Rockville, Md. on Jan. 31, 1989, under deposit accession number HB 10012.

The following Methods and Examples detail the preparation and characterization of monoclonal antibody H37c94, and its diagnostic utility for differentiating exposure of an individual to HIV-2 from HIV-1.

A. Synthesis of Synthetic Peptides

The peptide corresponding to sequence 604-636 of HIV-2 envelope protein was assembled on a resin support by stepwise solid phase synthesis (starting with the carboxyl terminal residue) according to the general procedure described by Baray and Merrifield (Gross & Meinehofer, eds., The Peptides, vol. 2 [Academic Press, New York, 1980]). A BOC-L-Asn-OCH$_2$-Pam resin was transferred to a reaction vessel of an Applied Biosystems synthesizer, Model 430A. Protected amino acids were double coupled in a stepwise manner to the resin support by preformed symmetric anhydride chemistry, except, in the cases of arginine, asparagine, and glutamine addition, wherein the DCC/HOBT protocol described by Konig and Geiger was used (Chem. Ber. (1970) 103:788–798). All $\alpha$-amino-terminal residues were protected by t-butyloxycarbonyl (t-BOC) linkage, and side chains of various amino acid residues were protected by the following groups: Thr, Bzl; His, Tos; Cys, 4MeBzl; Arg, Tos; Ser, Bzl; Asp, OBzl; Tyr, 2-Br-Z; Lys, 2-Cl-Z; Glu, OBzl. The amino acids tryptophan and methionine were used without any side chain protecting groups. After incorporation of tryptophan, indole was added at a concentration of 1% (w/v) to trifluoroacetic acid for removal of all subsequent $N^{\alpha}$-protecting (BOC) groups. After incorporation of methionine, ethanedithiol was also added to trifluoroacetic acid at a concentration of 0.25% (v/v).

The protected peptide-resin (300 mg) was allowed to swell in methylene chloride (CH$_2$Cl$_2$) for 5 minutes. The $N^{\alpha}$-BOC protecting groups were removed using 60% trifluoroacetic acid (TFA/CH$_2$Cl$_2$) containing indole and ethanediol, CH$_2$Cl$_2$ washes, 10% N,N-diisopropylethylamine (DIEA/CH$_2$Cl$_2$) neutralization, and final CH$_2$Cl$_2$ washes. The resin was dried in vacuo. The peptide-resin thus obtained was treated with 10 ml of anhydrous hydrofluoric acid (HF), to which 1 ml p-cresol and 1 ml dimethylsulfide had been added, for 60 minutes at 0° C. The HF was distilled off in vacuo at 0° C. The cleaved, free peptide and resin were washed 3 times with 15 ml aliquots of diethyl ether. The peptide was then extracted six times with 10 ml aliquouts of 40% aqueous acetic acid. The combined aqueous extracts were lyophilized to provide the crude peptide for purification.

The crude peptide was purified by reversed-phase HPLC on C$_4$ columns, employing gradients of 0.1% TFA/water (A) and 100% acetonitrile (B) as the solvent systems at a flow rate of 1 ml/min for the analytical column (Vydac-214-TP54, Vydac Separation Group, Hesperia, Calif.) or 12 ml/min for the semi-preparative one (Vydac-214-TP1022). The gradient was started with 30% B. After 3 minutes, the gradient was linearly increased to 40% B during 20 minutes, then brought back to 30% B in 1 minute.

The presence of peptide was monitored at 225 nm and 280 nm. The composition of the peptide was confirmed by hydrolysis in 6N hydrochloric acid/0.3% phenol at 150° C. for 2 hours in vacuo, and subsequently analyzed on a Beckman 6300 amino acid analyzer.

The peptide corresponding to sequence 577–607 of HIV-2 envelope protein was assembled as described above. After incorporation of tryptophan, indole was added at a concentration of 1 mg/ml to trifluoroacetic acid for removal of all subsequent $N^\alpha$-protecting groups (t-BOC). Three hundred twenty milligrams of the protected peptide-resin was treated with 8.5 ml of anhydrous hydrofluoric acid (HF), to which 0.5 ml p-cresol, 0.5 g p-thiocresol and 0.5 ml dimethylsulfide had been added. The crude peptide was purified starting with a gradient of 28% B, which after 3 minutes was linearly increased to 45% B in 23 minutes. It was then reduced back to 28% B over a period of 1 minute.

B. Immunization

Five Balb mice were immunized with HIV-2 gp41 peptide 604–636. Five hundred micrograms of p604–636 were mixed with RIBI adjuvant (RIBI Immunochem. Research Inc.) containing 500 μg detoxified endotoxin and 500 μg trehalose dimycolate (reconstituted in chloroform/methanol as described by the manufacturer). Squalane (20 μl) was added, the mixture was homogenized, and then water containing 0.2% Tween 20 was added to a final volume of 1.2 ml.

On day 1, each mouse received 0.1 ml subcutaneously (s.c.) and 0.1 ml intraperitoneally (i.p.) to receive in total approximately 100 μg of p604–636. The second immunization was conducted 8 weeks later when each mouse received 50 μg of p604–636, prepared by mixing 250 μg p604–636 with 250 μg of the RIBI adjuvant, as described above. For the 3rd, 4th and 5th immunizations, at 20, 23 and 29 weeks after the first immunization, respectively, mice were immunized i.p. and s.c. with approximately 34, 25 and 25 μg of p604–636 in RIBI adjuvant, respectively. Mice were bled five days after the fourth immunization. The immune responses of the immunized mice were assessed by assaying their sera for anti-HIV-2 antibodies by an enzyme-linked immunoassay described hereinafter. Four weeks later, one particular mouse was immunized with 100 μl of 1 mg/ml p604–636 in 150 μl sterile water by tail vein injection. Three days later, the mouse was sacrificed for fusion.

C. Preparation of Microtiter Plates

Solutions of 1.0 μg/ml p577–607 and 1.0 μg/ml p604–636 were prepared using bicarbonate buffer, pH 9.6. Microtiter plates were coated overnight with 100 μl per well of either the p577–607 or p604–636 solution at room temperature. The plates were washed with bicarbonate buffer, then coated with 200 μl per well of 1% bovine serum albumin (BSA) in bicarbonate buffer for 3 hours at room temperature. The plates were washed three times with phosphate buffered saline (PBS) containing 0.05% Tween 20 and 0.01% sodium dodecyl sulfate (SDS).

D. Enzyme-linked Immunoassay (EIA)

Sera from naive or immunized mice were serially diluted using 20 mM potassium phosphate buffer, pH 7.4, containing 0.15M NaCl, 10% fetal calf serum (FCS), 10% normal goat serum (NGS) and 0.5% Triton X-100. The diluted sera were added to the wells of the microtiter plates prepared above, coated with either p577–607 or p604–636. The plates containing the sera were incubated for 30 minutes at 40° C., and then overnight at 4° C. The plates were washed ten times with PBS containing 0.05% Tween 20, before adding goat anti-mouse IgG (H+L) Horseradish Peroxidase (HRPO)-conjugated antibody (Jackson Laboratories) diluted 1:1000 in NGS. The plates were incubated for 1 hour at 40° C., washed ten times as described above, and o-Phenylenediamine:2HCl (OPD) color reagent was added. The reaction was stopped after 30 minutes by addition of 1N $H_2SO_4$, and the absorbance at 492 nm was determined. The absorbance was directly proportional to the amount of mouse antibody bound to the wells. These assays demonstrated the presence of antibody to HIV-2 p604–636 in the sera of the immunized mice. Mice immunized with p604–636 showed titers against p604–636 greater than 1:10,000. Antisera specific to p604–636 showed no cross reactivity against p577–607.

E. Cell Fusion

The spleen of the sacrificed mouse, containing the anti-HIV-2 antibody producing cells, was disrupted to single cells, by mashing through a wire screen into Dulbecco's Modified Eagle's Medium (DMEM), containing 2.0 mM L-glutamine and 50 μg/ml gentamicin. The single cell suspension was treated with 0.83% ammonium chloride-10 mM Tris (Tris[hydroxymethyl]aminomethane) to lyse the red blood cells, and then mixed with SP2/0 cells at a 1:1 ratio. The mixed cells were centrifuged, washed once with serum-free medium, then centrifuged again. The fusogen polyethylene glycol (PEG) was used to form hybrids of the immune donor spleen cells with the myeloma cell line SP2/0 (see G. Kohler and C. Milstein, Nature (1975) 256:494, and reviewed in *Monoclonal Hybridoma Antibodies: Techniques and Applications*, ed. J. G. R. Hurrell [CRC Press, Inc., 1982]). Briefly, fusion of the spleen and SP2/0 cells was accomplished by exposing the pellet to 50% PEG (Sigma, MW 1000) in serum-free DMEM for two minutes. The PEG was diluted by adding 1 ml of serum-free DMEM, waiting 1 minute and then slowly adding an additional 20 ml of serum-free DMEM over a period of five minutes. The cells were collected by centrifugation. The supernatant was decanted and replaced with 20 ml DMEM containing 20% FCS with HAT (hypoxanthine, aminopterin, and thymidine) to select for hybridomas. The cells were diluted to approximately $1 \times 10^6$ cells/ml and plated at 1 ml/well into 24 multiwell plates. Spleen cells from a non-immunized Balb/c mouse were also added as a feeder layer. Every other day, 1 ml of the media was replaced with fresh DMEM, containing 20% FCS with HAT, and hybrids were allowed to grow for an additional 7–14 days.

Some of the hybrids were composed of spleen cells making antibody to HIV-2 fused with SP2/0 cells. Briefly, the fusogen promotes fusion of spleen cell and SP2/0 cell membranes, forming a heterokaryon containing nuclei of both cells. Eventually, the dissimilar nuclei fuse producing a single nucleus capable of synchronous mitosis. As the fused cells divide, the hybrid stabilizes by losing chromosomes of each nuclei. The fused cells are plated into multiple 24 well plates at $10^5$ to $10^6$ cells per well. Hybrid cells formed from SP2/0:spleen cell fusions are selectively propagated by culturing in HAT medium. All unfused SP2/0 or SP2/0:SP2/0 fused cells are prevented from growing by aminopterin, and unfused spleen cells or spleen:- spleen fused cells die off in culture. Only SP2/0:spleen hybrids will grow in the HAT selection medium.

EXAMPLE 1

Screening, Cloning and Characterization of Monoclonal Antibody

Using the methods described above, hybrids were screened for antibody to HIV-2. After 10–14 days, culture fluids from the wells containing hybridoma cell growth were screened using the EIA procedure described in the methods, with the following changes in the protocol. The plates were incubated with the culture fluids for 3–4 hours at 40° C., then the plates were washed with PBS containing 0.05% Tween 20 and 0.1% SDS. All selected hybrids reacted strongly with p604–636 and were negative against p577–607.

In addition, Western blots of hybrids were tested, using HIV-1 gag/HIV-2 gp41 (gag-p41) fusion protein and CKS-HIV-2 TMP fragment (CKS-TMP, containing the first 108 amino acids of HIV-2 TMP) fusion protein as the target antigens. These proteins were prepared as disclosed in coassigned and copending patent applications U.S. Ser. Nos. 275309 and 276263, filed Nov. 23, 1988, which are incorporated herein by reference. Briefly, 500 µl of gag-p41 were treated with SDS and 2-mercaptoethanol at 95° C., and electrophoresed in a 10% polyacrylamide-SDS gel (Laemmli et al., Nature (1970) 227:680–685). Similarly, 250 µl of 2 mg/ml solution of partially purified CKS-TMP were treated with SDS and 2-mercaptoethanol at 95° C., and electrophoresed in a 12% polyacrylamide-SDS gel. Proteins were transferred overnight from the gel to nitrocellulose by electrophoresis at 100 mamp, or transferred in 1–2 hours at 1.0 amp, in standard transfer buffer composed of 25 mM Tris, 192 mM glycine, and 2.0% methanol, pH 8.3. (Towbin et al., Proc. Natl. Acad. Sci. (1979) 76:4350–4354.) After transferring the recombinant proteins and blocking the nitrocellulose with 20% FCS in 10 mM Tris (pH 8.0) containing 0.15 M NaCl, the nitrocellulose was cut into strips which were used to determine the presence of anti-HIV-2 antibodies.

For Western blot procedures, reaction mixtures consisted of a nitrocellulose strip incubated with 0.2 ml of the selected hybrid and 1.8 ml of buffer (20 mM Tris, 1 mM EDTA, 0.2 M NaCl, 0.3% Triton X-100, and 2 mg/ml BSA, pH 7.5) overnight at 4° C. The strips were washed with buffered detergent (10 mM PBS, pH 7.5, containing 0.1% SDS and 0.5% Triton X-100, alternated with PBS containing 0.5M NaCl and 0.5% Triton X-100), followed by addition of goat anti-mouse IgG antibody conjugated to HRPO. The strips were incubated for 1–2 hours at room temperature, followed by washing with buffered detergent. Finally, antibody bound to the recombinant protein was visualized by addition of freshly prepared HRP color reagent (Biorad) (120 mg dissolved in 40 ml ice-cold methanol, then diluted into 200 ml Tris buffered saline, pH 7.8, containing 120 µl of 30% hydrogen peroxide). This assay demonstrated the presence of antibody specific to HIV-2 proteins. Two hybrids, including H37, showed blot reactivity with both gag-p41 and CKS-TMP. The rest of the hybrids showed reactivity with only gag-p41.

The hybrids were expanded by limiting dilution using the guidelines outlined by J. W. Goding in *Monoclonal Antibodies: Principles and Practice* (Academic Press, New York, 1983). Briefly, the hybrids were expanded into 2-96 multiwell plates at one cell/well, and allowed to grow for about two weeks. From a single hybrid H37, 46 wells were identified which contained cell growth and colony formation. Culture fluid from each well was screened by EIA and Western blot. Of the 46 wells, 3 were identified as positive for anti-HIV-2 antibody. Cells from each of these 3 were expanded into 24 multiwell plates, and then further expanded into 25 cm$^2$, followed by, 75 cm$^2$ flasks. Of the 3 expanded clones, one was designated H37c94.

The isotype of monoclonal antibody H37c94 was determined to be IgG2a. The EIA isotyping procedure employed a microtiter plate coated with goat anti-mouse IgG immunoglobulin, which was incubated with culture fluid of the clone to capture the secreted mouse antibody. After 2 hours, the plate was washed, then rabbit anti-mouse isotype was applied for an additional 2 hr. The plate was washed again, and HRPO-conjugated goat anti-rabbit IgG was applied for 1 hr. The excess conjugate was removed by washing, then OPD substrate was added. The amount of rabbit anti-mouse isotype bound to the mouse immunoglobulin was proportional to the absorbance measured at 492 nm. Further characterization was performed with H37c94 antibody from mouse ascites.

In order to obtain greater amounts of H37c94 monoclonal antibody, the H37c94 clone was amplified in mice. Ten to twenty million cloned H37c94 cells were innoculated into a Balb/c mouse previously treated intraperitoneally with 0.5 ml pristane (2,6,10,14-tetramethylpentadecane)[method outlined in Hurrell, supra]. Pristane treatment enhances growth of mouse myeloma hybrids within the peritoneum of the mouse, and the ascites fluids which form are rich in the monoclonal antibody secreted by the hybrid cells. After formation of monoclonal antibody-enriched ascites, the mice were sacrificed, and the ascites withdrawn from the peritoneum was clarified by centrifugation. Characterization procedures described hereinafter were performed with the clarified ascites fluid or purified antibodies from the ascites, using purification procedures known in the art, including Protein A-Sepharose (Hurrell, supra).

Determination of Activity and Specificity

Assays were performed to determine the titer of monoclonal antibody in mouse ascites and to assess the specificity of the monoclonal antibody. The monoclonal antibody in the ascites was titered by EIA; using the procedure previously described. The plates were incubated with the ascites fluid for 1 hour at 40° C. The monoclonal antibody-enriched ascites exhibited high titers, greater than 1:500,000, against the synthetic peptide p604–636. The ascites showed no reactivity against p577–607.

In addition, the specificity of the monoclonal antibody H37c94 was confirmed by radioimmunoprecipitation assays (RIPA). Immunoprecipitation assays for viral proteins have been described previously (Devare et al., Proc. Natl. Acad. Sci., U.S.A., (1986), 83: 5718–5722). Cell lines employed for these studies were uninfected H9 cells or HIV-2 infected H9 cells. Cells were harvested from culture, washed once with RPMI 1640 deficient in methionine and cysteine (Gibco Laboratories), then suspended at 1–2.5×10$^6$ cells/ml in the same medium. Washed cells were incubated for 30–45 min. at 37° C. in 6% CO$_2$, followed by addition of 50–100 µCi each of [$^{35}$S]methionine and [$^{35}$S]cysteine (Amersham) to the medium. Cells were radiolabeled at 37° C. for 4–8 hr, harvested by centrifugation, and lysed in PBS, pH 7.4, containing I mM PMSF, aprotinin (100 Kallikrein inactivation units per ml of buffer), 1.0% Triton X-100, 0.1% SDS, and 0.5% sodium deoxycholate (all reagents from Sigma). The lysate was clarified by centrifugation at 100,000×g for 40 min. and stored at −70° C.

Immunoprecipitation was performed by incubating 100 μl aliquots of cell lysates with 10 μl of monoclonal antibody-enriched ascites or 100 μl of tissue culture fluid for 30–60 minutes at 4° C. Antibody-antigen complexes were recovered by addition of 200 μl of preswollen Protein A-Sepharose (Pharmacia, IgG binding capacity of 50–200 μg/200 μl Protein A) previously washed in lysis buffer containing 1 mg/ml BSA. The reaction mixture was shaken vigorously at 4° C. for 1 hr, followed by 3 washes of the Protein A-Sepharose using lysis buffer. Protein A-Sepharose was then collected by centrifugation, and immune complexes were dissociated by heating at 95° C. in SDS gel sample buffer containing 2-mercaptoethanol (Laemmli et al., supra). The sample was subjected to SDS-10% polyacrylamide gel electrophoresis. The gel was incubated for 30 min. in Enhance (Dupont), dried, and exposed to x-ray film for autoradiography of the immunoprecipitated, radiolabeled proteins. The specificity of H37c94 antibody to an epitope within HIV-2 gp41 was confirmed by immunoprecipitation of [35S]methionine/[35S]cysteine biosynthetically-labeled viral glycoproteins gp160 (uncleaved envelope precursor) and gp41 from HIV-2 infected H9 cell lysates. The results indicated that gp160 and gp41, but not gp120, were precipitated from HIV-2 infected cell lysates by the monoclonal antibody, and that there was no detectable nonspecific immunoprecipitation of any radiolabeled cellular proteins. Thus, the monoclonal antibody H37c94 specifically bound HIV-2 gp160/41. The banding pattern showed precipitation of gp160, gp41 and minor bands (possible fragments of gp41) corresponding to bands precipitated with HIV-2 seropositive sera, and confirming reports by other researchers of other HIV-2 transmembrane proteins. H37c94 recognizes the same proteins as those seen by HIV-2 seropositive individuals.

EXAMPLE 2

Mapping and Characterization of the Epitope Recognized by Monoclonal Antibody H37c94

It was established by the EIA screening of hybrids that H37c94 did not recognize p577–607. In addition, H37c94 ascites fluid recognized the CKS-HIV-2 TMP fragment fusion protein in the Western blot procedures.

The amino acid sequence of the immunizing peptide p604–636 is:

HTTVPWVNDSLAPDWDNMTWQEWEKQ-
VRYLEAN

The sequence of the non-cross reactive peptide p577–607 is:

ARVTAIEKYLQDQARLNSW-
GCAFRQVCHTTV

The sequence of the CKS-HIV-2 TMP fragment fusion protein is:

YSS...
WDWARLNSWGCAFRWVCHTTVPW/ST-
LEDPRV...

(The amino acids after the slash are non-sense coding in the clone.)

Monoclonal antibody H37c94 recognizes an epitope having the amino acid sequence HTTVPW, common to both the immunizing peptide and the fusion protein. The overlap of 6 identical amino acids between the immunizing peptide and the fusion protein provides an epitope that H37c94 recognizes. The sequence HTTV of p577–607 is not sufficient to form the epitope that H37c94 recognizes.

HTTVPWVNDSLAPDWDNMTWQEWEKQVRYLEAN
YSS...WDWARLNSWGCAFRWVCHTTVPW/STLEDPRV...

In addition, a comparison of the sequence in the corresponding region of HIV-1 reveals that 2 of the 6 amino acids are different. This change is sufficient to prevent H37c94 from recognizing HIV-1 gp41.

HIV-2 ...HTTVPW...
HIV-1 ...TTAVPW...

EXAMPLE 3

Differentiation of HIV-1 and HIV-2

In accordance with the present invention, H37c94 has been shown to be useful as a competitive probe for the detection of HIV-2 seropositive samples. Also accordance with the present invention, H37c94 can be utilized to differentiate exposure of an individual to HIV-2 from exposure to HIV-1 because it only competes with samples containing antibody to HIV-2gp41, and not samples containing HIV-1 gp41 antibody. HIV-1 seropositive sera do not readily compete with H37c94 in a competitive immunoassay, whereas HIV-2 seropositive sera do compete.

In a preferred configuration of the H37c94 competitive assay, the recombinant CKS-HIV-2 TMP fragment fusion protein was coated on a solid support and incubated with a test sample and monoclonal antibody H37c94. The HIV-2 virus-specific antibodies present in the test sample competed with H37c94 for binding to the recombinant protein on the solid support. The amount of H37c94 bound to the recombinant protein was quantitated by use of goat anti-mouse immunoglobulin conjugated to HRPO.

Serum samples, 15 HIV-1, 8 HIV-2, and 11 Dual, were tested by the method of the H37c94 competitive assay. Classification of sera as HIV-1, HIV-2, or DUAL (containing distinct and separate antibody populations to HIV-1 and HIV-2) was based on (1) the presence of antibody to the immunodominant regions of the transmembrane proteins of HIV-1 and HIV-2, as determined in a peptide inhibition assay explained herein, (2) the presence of antibody to exterior glycoproteins of HIV-1 and HIV-2 as determined either by radioimmunoprecipitation of biosynthetically radiolabeled viral proteins from infected cell lysates, or by analysis in Western blots using partially purified lysed viruses as the serological targets, and (3) the presence of antibody to the transmembrane proteins of both HIV-1 and HIV-2 as determined by either Western blot analysis using partially purified viruses as the serological targets, or by reactivity in an enzyme linked immunoassay employing recombinant transmembrane proteins as the serological targets. The recombinant proteins used were (1) a BglII to KpnI restriction fragment of gp41 for HIV-1 and a HIV-2 transmembrane protein fused to the E.coli protein CKS. Characterization of the sera are shown in Tables 1, 2, and 3. The data clearly indicate that the peptide inhibition assay is more reliable and less ambiguous than other methods for determining which serum samples react against HIV-1, HIV-2, or both viruses.

TABLE 1

Classification of HIV-1 samples.

| SAMPLE ID | IDR PEP[A] ASSAY | EGP RIPA[B] HIV-1 | EGP RIPA[B] HIV-2 | WESTERN BLOT[C] EGP HIV-1 | WESTERN BLOT[C] EGP HIV-2 | WESTERN BLOT[C] TMP HIV-1 | WESTERN BLOT[C] TMP HIV-2 | EIA[D] HIV-1 rTMP S/CO | EIA[D] HIV-1 rTMP TITER | EIA[E] HIV-2 rTMP S/CO | EIA[E] HIV-2 rTMP TITER |
|---|---|---|---|---|---|---|---|---|---|---|---|
| EW | HIV-1 | 4 | 0 | 3 | 0 | 3 | 0 | 9.5 | 512 | 1.5 | 2 |
| G-019724 | HIV-1 | 2 | 0 | 2 | 0 | 2 | 1 | 7.2 | 512 | 4.2 | 16 |
| G-019747 | HIV-1 | 4 | 0 | 2 | 0 | 2 | 1 | 8.8 | 4096 | 6.1 | 64 |
| G-019988 | HIV-1 | 2 | 0 | 2 | 0 | 2 | 1 | 7.9 | 4096 | 6.1 | 128 |
| G-018602 | HIV-1 | 2 | 0 | 2 | 0 | 2 | 1 | 9.0 | 2048 | 7.7 | 256 |
| G-012168 | HIV-1 | 0 | 0 | 0 | 0 | 2 | 0 | 8.7 | 512 | 5.1 | 64 |
| GA | HIV-1 | 4 | 0 | nd | nd | nd | nd | nd | nd | nd | nd |
| CAV* | nd | nd | nd | nd | nd | nd | nd | nd | nd | nd | nd |
| TS* | nd | nd | nd | nd | nd | nd | nd | nd | nd | nd | nd |
| RC* | nd | nd | nd | nd | nd | nd | nd | nd | nd | nd | nd |
| LJ* | nd | nd | nd | nd | nd | nd | nd | nd | nd | nd | nd |
| RM* | nd | nd | nd | nd | nd | nd | nd | nd | nd | nd | nd |
| MK* | nd | nd | nd | nd | nd | nd | nd | nd | nd | nd | nd |
| HH* | nd | nd | nd | nd | nd | nd | nd | nd | nd | nd | nd |
| 123* | nd | nd | nd | nd | nd | nd | nd | nd | nd | nd | nd |

*U.S. seropositive samples from Rush Presbyterian St. Luke's Medical Center, Chicago, IL, known to be HIV-1 positive.
nd not determined.
[A]Identity of these sera were determined using the peptide inhibition assay.
[B]Each serum was scored for reactivity against the exterior glycoprotein (EGP) of each virus by immunoprecipitation of biosynthetically radiolabeled EGP from HIV-1 or HIV-2 infected cell lysates. Numbers indicate the relative amount of glycoprotein precipitated, with 0 = no detectable precipitation and 4 = strong precipitation.
[C]Each serum was scored for reactivity against the exterior glycoprotein (EGP) and transmembrane glycoprotein (TMP) of each virus in Western blots employing partially purified HIV electrophoresed under non-reducing conditions. Numbers indicate the relative reactivity with 0 = no detectable reactivity and 4 = strong reactivity.
[D,E]Reactivity of each serum against a recombinant transmembrane protein (rTMP) from each virus was determined by a simple enzyme linked immunoassay (EIA) which reacted the serum sample against the rTMP bound to a solid phase, and antibody bound to the rTMP was detected using goat anti-human IgG coupled to horseradish peroxidase.

TABLE 2

Classification of HIV-2 samples.

| SAMPLE ID | IDR PEP[A] ASSAY | EGP RIPA[B] HIV-1 | EGP RIPA[B] HIV-2 | WESTERN BLOT[C] EGP HIV-1 | WESTERN BLOT[C] EGP HIV-2 | WESTERN BLOT[C] TMP HIV-1 | WESTERN BLOT[C] TMP HIV-2 | EIA[D] HIV-1 rTMP S/CO | EIA[D] HIV-1 rTMP TITER | EIA[E] HIV-2 rTMP S/CO | EIA[E] HIV-2 rTMP TITER |
|---|---|---|---|---|---|---|---|---|---|---|---|
| 8669 | HIV-2 | 0 | 2 | 0 | 1 | 0 | 3 | 2.5 | 16 | 10.3 | 512 |
| 13894 | HIV-2 | 0 | 2 | 0 | 4 | 0 | 2 | 2.6 | 2 | 13.6 | 1024 |
| 36207 | HIV-2 | 0 | 0 | 0 | 2 | 0 | 2 | 1.3 | 2 | 12.0 | 2048 |
| G-018511 | HIV-2 | 0 | 3 | 0 | 4 | 2 | 1 | 1.7 | 2 | 12.2 | 2048 |
| G-012181 | RIV-2 | 0 | 4 | 0 | 3 | 1 | 2 | 1.2 | 2 | 11.7 | 1024 |
| G-012292 | HIV-2 | 0 | 2 | 0 | 3 | 0 | 2 | <1 | 0 | 11.8 | 4096 |
| G-019821 | HIV-2 | 2 | 1 | 0 | 3 | 2 | 1 | 2.6 | 8 | 13.4 | 4096 |
| G-018451 | HIV-2 | 2 | 4 | 0 | 3 | 0 | 2 | 3.7 | 8 | 11.6 | 1024 |

[A]Identity of these sera were determined using the peptide inhibition assay as show in FIG. 2.
[B]Each serum was scored for reactivity against the exterior glycoprotein (EGP) of each virus by immunoprecipitation of biosynthetically radiolabeled EGP from HIV-1 or HIV-2 infected cell lysates. Numbers indicate the relative amount of glycoprotein precipitated, with 0 = no detectable precipitation and 4 = strong precipitation.
[C]Each serum was scored for reactivity against the exterior glycoprotein (EGP) and transmembrane glycoprotein (TMP) of each virus in Western blots employing partially purified HIV electrophoresed under non-reducing conditions. Numbers indicate the relative reactivity with 0 = no detectable reactivity and 4 = strong reactivity.
[D,E]Reactivity of each serum against a recombinant transmembrane protein (rTMP) from each virus was determined by a simple enzyme linked immunoassay (EIA) which reacted the serum sample against the rTMP bound to a solid phase, and antibody bound to the rTMP was detected using goat anti-human IgG coupled to horseradish peroxidase.

fusion protein comprising the amino terminal ⅔ of

TABLE 3

Characterization of Dual samples.

| SAMPLE ID | IDR PEP[A] ASSAY | EGP RIPA[B] HIV-1 | EGP RIPA[B] HIV-2 | WESTERN BLOT[C] EGP HIV-1 | WESTERN BLOT[C] EGP HIV-2 | WESTERN BLOT[C] TMP HIV-1 | WESTERN BLOT[C] TMP HIV-2 | EIA[D] HIV-1 rTMP S/CO | EIA[D] HIV-1 rTMP TITER | EIA[E] HIV-2 rTMP S/CO | EIA[E] HIV-2 rTMP TITER |
|---|---|---|---|---|---|---|---|---|---|---|---|
| G-019862 | DUAL | 1 | 2 | 1 | 3 | 2 | 1 | 4.1 | 128 | 9.6 | 8192 |
| 19053 | DUAL | 2 | 2 | 2 | 2 | 2 | 2 | 7.9 | 32 | 13.1 | 2048 |
| SENEGAL 1 | DUAL | 4 | 3 | 3 | 2 | 2 | 1 | 7.3 | 1024 | 11.7 | 8192 |
| SENEGAL 2 | DUAL | 4 | 3 | 3 | 2 | 2 | 1 | 7.4 | 1024 | 11.2 | 2048 |
| G-018450 | DUAL | 3 | 3 | 2 | 3 | 2 | 1 | 7.3 | 512 | 15.0 | 2048 |
| G-018758 | DUAL | 2 | 4 | 2 | 3 | 2 | 1 | 7.3 | 2048 | 13.5 | 8192 |

TABLE 3-continued

| | | | | | Characterization of Dual samples. | | | | | |
|---|---|---|---|---|---|---|---|---|---|---|
| | | | | WESTERN BLOT[C] | | | | EIA[D] | | EIA[E] | |
| SAMPLE | IDR PEP[A] | EGP RIPA[B] | | EGP | | TMP | | HIV-1 rTMP | | HIV-2 rTMP | |
| ID | ASSAY | HIV-1 | HIV-2 | HIV-1 | HIV-2 | HIV-1 | HIV-2 | S/CO | TITER | S/CO | TITER |
| G-018564 | DUAL | 2 | 1 | 2 | 3 | 2 | 1 | 8.2 | 1024 | 11.0 | 1024 |
| G-018459 | DUAL | 0 | 2 | 2 | 3 | 2 | 1 | 6.4 | 512 | 14.7 | 4096 |
| G-018790 | DUAL | 0 | 2 | 1 | 3 | 2 | 1 | 6.7 | 64 | 11.5 | 512 |
| G-018528 | DUAL | 0 | 1 | 2 | 3 | 2 | 1 | 7.9 | 2048 | 13.4 | 1024 |
| G-018771 | DUAL | 0 | 4 | 1 | 3 | 2 | 1 | 6.7 | 128 | 10.8 | 2048 |

[A]Identity of these sera were determined using the peptide inhibition assay as show in FIG. 2.
[B]Each serum was scored for reactivity against the exterior glycoprotein (EGP) of each virus by immunoprecipitation of biosynthetically radiolabeled EGP from HIV-1 or HIV-2 infected cell lysates. Numbers indicate the relative amount of glycoprotein precipitated, with 0 = no detectable precipitation and 4 = strong precipitation.
[C]Each serum was scored for reactivity against the exterior glycoprotein (EGP) and transmembrane glycoprotein (TMP) of each virus in Western blots employing partially purified HIV electrophoresed under non-reducing conditions. Numbers indicate the relative reactivity with 0 = no detectable reactivity and 4 = strong reactivity.
[D,E]Reactivity of each serum against a recombinant transmembrane protein (rTMP) from each virus was determined by a simple enzyme linked immunoassay (EIA) which reacted the serum sample against the rTMP bound to a solid phase, and antibody bound to the rTMP was detected using goat anti-human IgG coupled to horseradish peroxidase.

In the H37c94 competitive assay, an absorbance value which was equal to the sum of the absorbance of the positive control and the negative control divided by two, was considered the cutoff value. Samples showing higher absorbance values than the cutoff value were not considered to compete with H37c94 and were classified "Non-HIV-2". Samples showing lower absorbance values than the cutoff value were considered to compete with H37c94 and were classified "HIV-2". Therefore, "Non-HIV-2" sera have a sample to cutoff absorbance value (S/CO) greater than or equal to 1.0, and "HIV-2" sera have a S/CO less than 1.0.

As shown in Table 4, the competitive assay utilizing H37c94 as a probe is an effective method for differentiating between HIV-2 and HIV-1 seropositive samples. The specificity of H37c94 for HIV-2 gp41 was demonstrated by its lack of competition with anti-HIV-1 antibodies. All 15 HIV-1 samples were identified in the H37c94 competitive assay as "Non-HIV-2". Of the 8 HIV-2 samples, all were correctly identified. Those samples classified as dual were detected by the competitive assay and identified as "HIV-2".

In addition, by contrasting Table 4 to Tables 1-3, we demostrate that the H37c94 competitive assay performs in a superior manner as a differentiation reagent when compared to radioimmunoprecipitation, Western blot, or ELISA using recombinant proteins. Finally, it is important to note the 100% agreement between the H37c94 competitive assay and the peptide inhibition assay.

TABLE 4

| SERA CLASSIFICATION | SERA ID | H37c94 S/CO | COMPETITIVE ASSAY CLASSIFICATION |
|---|---|---|---|
| HIV-1 | G-012168 | 1.5 | NON-HIV-2 |
| | G-018602 | 1.1 | NON-HIV-2 |
| | G-019724 | 1.5 | NON-HIV-2 |
| | G-019747 | 1.3 | NON-HIV-2 |
| | G-019988 | 1.0 | NON-HIV-2 |
| | CAV | 1.6 | NON-HIV-2 |
| | EW | 1.5 | NON-HIV-2 |
| | GA | 1.3 | NON-HIV-2 |
| | TS | 1.3 | NON-HIV-2 |
| | RC | 1.4 | NON-HIV-2 |
| | LJ | 1.6 | NON-HIV-2 |
| | RM | 1.5 | NON-HIV-2 |
| | MK | 3.2 | NON-HIV-2 |
| | HH | 1.5 | NON-HIV-2 |
| | 123 | 1.5 | NON-HIV-2 |
| HIV-2 | 8669 | 0.75 | HIV-2 |
| | 13894 | 0.70 | HIV-2 |
| | 36207 | 0.73 | HIV-2 |

TABLE 4-continued

| SERA CLASSIFICATION | SERA ID | H37c94 S/CO | COMPETITIVE ASSAY CLASSIFICATION |
|---|---|---|---|
| | G-018511 | 0.58 | HIV-2 |
| | G-012181 | 0.69 | HIV-2 |
| | G-012292 | 0.57 | HIV-2 |
| | G-019821 | 0.50 | HIV-2 |
| | G-018451 | 0.69 | HIV-2 |
| DUAL | G-019862 | 0.23 | HIV-2 |
| | 19053 | 0.69 | HIV-2 |
| | SENEGAL-1 | 0.38 | HIV-2 |
| | SENEGAL-2 | 0.42 | HIV-2 |
| | G-018450 | 0.46 | HIV-2 |
| | G-018758 | 0.51 | HIV-2 |
| | G-018564 | 0.80 | HIV-2 |
| | G-018459 | 0.48 | HIV-2 |
| | G-018790 | 0.73 | HIV-2 |
| | G-018528 | 0.64 | HIV-2 |
| | G-018771 | 0.65 | HIV-2 |

Additionally, 63 specimens from a normal population were screened using the H37c94 competitive assay described above. The assay demonstrated a mean S/CO value of 1.6 (SD=0.114, CV=7.2%).

Peptide Inhibition Assay Method

Sera were determined to be from HIV-1, or HIV-2, or Dually infected (HIV-1 and HIV-2) individuals using a peptide inhibition assay which employed synthetic polypeptides derived from the immunodominant regions (IDR) of the transmembrane proteins of HIV-1 and HIV-2. Synthetic polypeptides, either HIV-1 IDR or HIV-2 IDR, were solubilized in 88% formic acid and diluted to 5 μg/ml in 0.1M Tris buffer containing 0.5M NaCl and 0.0022% Triton X-100, and the pH was adjusted to 8.5. The peptides were incubated with polystyrene beads for 2 hours at 37° C. The beads were washed with 0.1% Triton in PBS, pH 7.4, for 1 hour at 40° C. The beads were washed with PBS, coated with 5% BSA in PBS for 1 hour at 40° C., washed with PBS, and coated with 5% sucrose in PBS for 20-30 minutes at room temperature. The IDR coated beads were employed as serological targets in the peptide inhibition assay. Each serum sample was titrated against each type of bead to optimize sensitivity of the peptide inhibition assay. Each serum sample (at the previously determined optimal dilution) was pre-incubated with each free HIV IDR peptide prior to addition of the entire mixture to each IDR coated bead. Ten microliters of each serum sample was added to two different concentrations of each HIV-1 or HIV-2 IDR peptide in separate reaction mixtures, containing either 0.3 nmole or 3.0 nmole of free IDR peptide in a diluent composed of 11 nM sodium phosphate buffer, 0.09M NaCl, 0.2% Triton X-100, 20% NGS, and 10% FCS, final volume 400 μl. Finally, each reaction mixture containing sample and free IDR polypeptide, as well as a mixture containing sample without free IDR polypeptide, was reacted against the HIV-1 IDR and HIV-2 IDR coated beads. After a one hour incubation, the beads were washed, and the amount of human antibody to the IDR fixed to the bead was determined using HRP labeled goat anti-human IgG and an appropriate substrate.

EXAMPLE 4

In addition to H37c94, a second mouse monoclonal antibody, 5-21-3, specific for HIV-1 gp41 (Abbott Case No. 4573.US.01, Ser. No. 176,077 filed Mar. 30, 1988) also may be employed in a simialr manner to detect HIV-1 samples and differentiate them from HIV-2 samples. In this example, each sample is reacted in two competitive assays, one of which would employ 5-21-3 as the competitive monoclonal with the HIV-1 transmembrane protein (TMP) as the serological target and the other would employ H37c94 as the competitive monoclonal (FIG. 1a) with the HIV-2 transmembrane protein as the serological target. Samples containing antibody to HIV-1 transmembrane protein compete with 5-21-3 and not H37c94, and samples containing antibody to HIV-2 transmembrane protein compete with H37c94 and not 5-21-3. Samples which contain antibody to both transmembrane proteins compete with both monoclonals. The data presented in Table 5 illustrate this example precisely. In Table 5, positive samples which compete against either monoclonal antibody yield a sample: cutoff ratio of less than 1.0, whereas samples which do not compete against either monoclonal yield sample:cutoff ratios of greater than 1. Monoclonal 5-21-3 is competed only by the sample characterized as HIV-1 or DUAL, and not by the samples characterized as HIV-2. In contrast, monoclonal H37c94 is competed only by those samples characterized as HIV-2 or DUAL, and not by HIV-1 samples. In the case of H37c94, full length HIV-2 TMP may provide a better target and increase the ability of HIV-2 sera to compete against H37c94. Two-monoclonal, competitive immunoassays, which together identify and discriminate HIV-1 positive samples vs. HIV-2 positive samples vs. DUAL positive samples can be summarized as follows:

TABLE 5

CORRELATION OF MONOCLONAL COMPETITIVE ASSAY WITH IDR PEPTIDE INHIBITION ASSAY

| SAMPLE ID | IDR PEP ASSAY | 5-21-3 ASSAY[A] S/CO | H37C94 ASSAY[B] S/CO | H37C94 ASSAY[C] S/CO |
|---|---|---|---|---|
| SA | HIV-1 | 0.10 | 1.54 | ND |
| SM | HIV-1 | 0.148 | 1.77 | ND |
| 86240003 | HIV-1 | 0.326 | 1.76 | ND |
| 86240004 | HIV-1 | 0.184 | 1.76 | ND |
| 86240010 | HIV-1 | 0.088 | 1.92 | ND |
| 86240011 | HIV-1 | 0.145 | 2.02 | ND |
| 86239040 | HIV-1 | 0.095 | 1.54 | ND |
| EW | HIV-1 | 0.176 | 1.55 | ND |
| TA | HIV-1 | 0.290 | 1.79 | ND |
| GD215 | HIV-1 | 0.093 | 1.83 | ND |
| PA | HIV-1 | 0.121 | 1.87 | ND |
| HU | HIV-1 | 0.134 | 2.01 | ND |
| G-018387 | HIV-1 | 0.152 | 1.76 | ND |
| G-018611 | HIV-1 | 0.163 | 2.05 | ND |
| G-019546 | HIV-1 | 0.157 | 1.48 | ND |
| G-019051 | HIV-1 | 0.103 | 1.67 | ND |
| G-019724 | HIV-1 | 0.123 | 2.22 | ND |
| G-019747 | HIV-1 | 0.145 | 1.80 | ND |
| G-019988 | HIV-1 | 0.208 | 1.29 | ND |
| G-018602 | HIV-1 | 0.142 | 1.17 | ND |
| BU | HIV-1 | 0.224 | 1.91 | ND |
| G-018802 | HIV-1 | 0.267 | 1.94 | ND |
| G-012168 | HIV-1 | 0.330 | 1.76 | ND |
| G-019559 | HIV-1 | 0.147 | 1.16 | ND |
| G-019809 | HIV-1 | 0.132 | 1.86 | ND |
| 7185 | HIV-2 | 1.76 | 1.53 | 0.516 |
| 8669 | HIV-2 | 1.78 | 0.929 | 0.516 |
| 13894 | HIV-2 | 1.86 | 0.562 | 0.394 |
| 13925 | HIV-2 | 1.81 | 1.21 | 0.624 |
| 36207 | HIV-2 | 2.09 | 1.00 | 0.218 |
| SENEGAL 4 | HIV-2 | 1.60 | 0.765 | 0.225 |
| G-018511 | HIV-2 | 1.61 | 0.488 | 0.193 |
| G-012181 | HIV-2 | 1.27 | 0.836 | 0.360 |
| P01718819 | HIV-2 | 1.83 | 0.921 | 0.259 |
| G-012292 | HIV-2 | 1.52 | 0.549 | 0.203 |
| 14106 | HIV-2 | 1.59 | 0.658 | 0.318 |
| G-019821 | HIV-2 | 1.22 | 0.457 | 0.162 |
| G-018451 | HIV-2 | 1.24 | 0.611 | 0.178 |
| 12805 | DUAL | 0.220 | 1.255 | 0.306 |
| 19053 | DUAL | 0.837 | 0.876 | 0.218 |
| SENEGAL 1 | DUAL | 0.194 | 0.452 | 0.325 |
| SENEGAL 2 | DUAL | 0.322 | 0.700 | 0.290 |
| G-018450 | DUAL | 0.158 | 0.460 | 0.269 |
| G-018758 | DUAL | 0.133 | 0.623 | 0.166 |
| G-018564 | DUAL | 0.143 | 0.843 | 0.288 |
| G-018459 | DUAL | 0.261 | 0.558 | 0.206 |
| G-018790 | DUAL | 0.316 | 0.770 | 0.510 |
| G-018528 | DUAL | 0.122 | 0.836 | 0.431 |
| G-018771 | DUAL | 0.260 | 0.558 | 0.196 |

[A]Serological target was full length recombinant HIV-1 p41.
[B]Serological target was amino ½ recombinanat HIV-2 transmembrane protein.
[C]Serological target was full length recombinant HIV-2 transmembrane protein.

| Sample | HIV-1 | + | − |
|---|---|---|---|
| | HIV-2 | − | + |
| | Dual (HIV-1 + HIV-2) | + | + |

While specific examples have been given to illustrate the invention, it is to be understood that those skilled in the art will recognize variations without departing from the spirit and scope of the invention.

What is claimed is:

1. A monoclonal antibody which recognizes an epitope of a HIV-2 gp41 antigen comprising the amino acid sequence HTTVPW but which does not bind to HIV-1, and whose binding to said epitope depends on the binding of the antigen combining site of the antibody to the amino acid residues present in the amino acid sequence HTTVPW.

2. The monoclonal antibody of claim 1 produced by ATCC Deposit No. HB 10012.

3. A hybridoma cell line producing a monoclonal antibody which recognizes an epitope of a HIV-2 gp41 antigen comprising the amino acid sequence HTTVPW but which does not bind to HIV-1, and whose binding to said epitope depends on the binding of the antigen combining site of the antibody to the amino acid residues present in the amino acid sequence HTTVPW.

4. The hybridoma cell line of claim 3, wherein said cell line is ATCC Deposit No. HB 10012.

5. A peptide, consisting of an amino acid sequence HTTVPW which specifically binds antibody to HIV-2 but which does not bind antibody to HIV-1.

6. A competitive assay for differentiating HIV-2 infection from HIV-1 infection, comprising the steps of:
   a. contacting a biological sample with (i) a monoclonal antibody, which recognizes an epitope of a HIV-2 gp41 antigen comprising the amino acid sequence HTTVPW but which does not bind to HIV-1, and whose binding to said epitope depends on the binding of the antigen combining site of the antibody to the amino acid residues present in the amino acid sequence HTTVPW, and (ii) with a solid phase to which has been attached a recombinant or native HIV-2 gp41 protein containing said sequence, thereby forming a mixture;
   b. incubating said mixture for a time and under conditions sufficient to form complexes of monoclonal antibody/solid phase and/or biological sample/solid phase; and
   c. determining the amount of monoclonal antibody bound to said solid phase as an indication of exposure to HIV-2.

7. The method of claim 6, wherein said monoclonal antibody is produced by ATCC Deposit No. HB 10012.

8. The method of claim 6, wherein said monoclonal antibody is labeled with a detectable label.

9. A method for detecting HIV-2 infection comprising reacting a test sample with one or more reagents selected from the group consisting of (i) a monoclonal antibody, which recognizes an epitope of a HIV-2 gp41 antigen comprising the amino acid sequence HTTVPW but which does not bind to HIV-1, and whose binding to said epitope depends on the binding of the antigen combining site of the antibody to "said" the amino acid residues present in the amino acid sequence HTTVPW, and (ii) an antigen comprising the amino acid sequence HTTVPW which specifically binds to HIV-2 but which does not bind to HIV-1.

10. A method for determining the presence of antibody to HIV-2 gp41 in a biological sample, comprising the steps of:
    a. contacting the sample with an antigen consisting of the amino acid sequence HTTVPW, whereby an antigen/antibody complex is formed; and
    b. determining the amount of said complex formed as an indication of the presence of antibody to HIV-2 gp41 in the sample.

11. A kit for use in detecting exposure of an individual to HIV-2, comprising a container of monoclonal antibody which recognizes an epitope of a HIV-2 gp41 antigen comprising the amino acid sequence HTTVPW but which does not bind to HIV-1, and whose binding to said epitope depends on the binding of the antigen combining site of the antibody to the amino acid residues present in the amino acid sequence HTTVPW.

12. A kit for use in detecting exposure of an individual to HIV-2, comprising a container of immobilized antigen which specifically binds antibody to HIV-2 gp41 but which does not bind antibody to HIV-1, wherein said antigen consists of the amino acid sequence HTTVPW.

* * * * *